United States Patent

Wick et al.

[11] Patent Number: 4,515,814
[45] Date of Patent: May 7, 1985

[54] 3-PHENOXYPROPAN-2-OL DERIVATIVES FOR TREATING GLAUCOMA

[75] Inventors: Alexander E. Wick, Saint Nom La Breteche; Jean Binet, Breuillet, both of France

[73] Assignee: Synthelabo, Paris, France

[21] Appl. No.: 412,962

[22] Filed: Aug. 30, 1982

[30] Foreign Application Priority Data

Sep. 10, 1981 [FR] France ................................ 81 17137

[51] Int. Cl.³ ..................... A61K 31/135; C07C 91/32; C07C 91/34
[52] U.S. Cl. ..................................... 514/652; 564/349; 514/913
[58] Field of Search .......................... 424/330; 564/349

[56] References Cited

U.S. PATENT DOCUMENTS

| 3,723,476 | 3/1973 | Nakanishi et al. | 424/330 |
| 4,171,370 | 10/1979 | Jonas et al. | 564/349 |
| 4,252,984 | 2/1981 | Manoury et al. | 424/330 |

FOREIGN PATENT DOCUMENTS 2409980  7/1979  France ................................ 424/330

OTHER PUBLICATIONS

*Arch. int. Pharmaco dyn.*, vol. 143, 1963, pp. 299–330, Van Rossum et al., "Cumulative Dose–Response Curves".,

*Primary Examiner*—Natalie Trousof
*Assistant Examiner*—Patricia M. Scott
*Attorney, Agent, or Firm*—Wegner & Bretschneider

[57] ABSTRACT

New 3-phenoxypropan-2-ol derivatives of the formula:

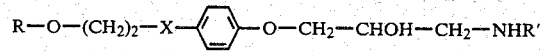

wherein R represents a cycloalkyl radical having 5 or 6 carbon atoms, X represents an oxygen atom or a bond, and R' represents the isopropyl or tert.-butyl radical, have been found to be useful in therapy, and more particularly in the treatment of cardiovascular diseases and glaucoma.

5 Claims, No Drawings

3-PHENOXYPROPAN-2-OL DERIVATIVES FOR TREATING GLAUCOMA

DESCRIPTION

The present invention relates to new therapeutically useful 3-phenoxypropan-2-ol derivatives, to processes for their preparation and pharmaceutical compositions containing them.

The 3-phenoxypropan-2-ol derivatives of the invention are those compounds of the general formula

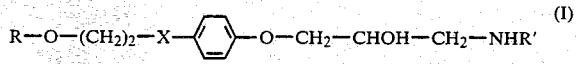
(I)

wherein R represents a cycloalkyl radical having 5 or 6 carbon atoms, X represents an oxygen atom or a bond, and R' represents the isopropyl or tert.-butyl radical, and pharmaceutically-acceptable acid addition salts thereof.

The compounds of general formula (I) have an asymmetric carbon atom; the racemates and enantiomers of compounds of general formula (I) form part of the present invention.

According to a feature of the present invention, the compounds of general formula (I) wherein X represents an oxygen atom are prepared by the process which comprises reacting a cycloalkyloxyethyl tosylate of the general formula:

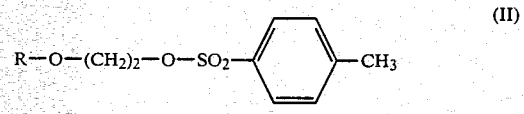
(II)

(wherein R is as hereinbefore defined) with 4-benzyloxyphenol to give a 1-cycloalkyloxyethoxy-4-benzyloxybenzene of the general formula:

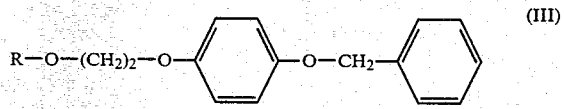
(III)

, debenzylating the compound to obtain a corresponding phenol of the general formula:

(IV)

, reacting the phenol with epichlorohydrin and, finally, reacting the epoxide so obtained of the general formula:

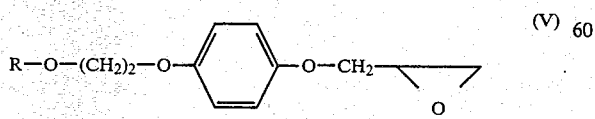
(V)

(wherein R is as hereinbefore defined) with an amine R'NH₂ (wherein R' is as hereinbefore defined) to give a compound of general formula (I) wherein X represents oxygen.

According to another feature of the invention, compounds of general formula (I) wherein X represents a bond are prepared by the process which comprises reacting 2-(4-benzyloxyphenyl)ethyl tosylate of the formula:

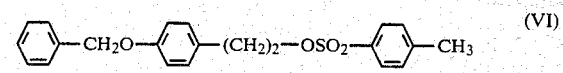
(VI)

with a sodium cycloalkanoate of the formula R-O-Na (wherein R is as hereinbefore defined), debenzylating the resulting compound of the general formula:

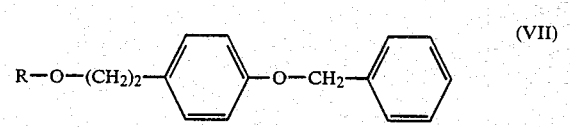
(VII)

to give a corresponding phenol of the general formula:

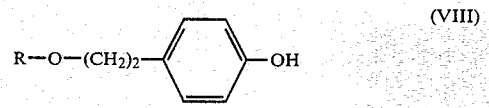
(VIII)

, reacting the phenol with epichlorohydrin to give a compound of the general formula:

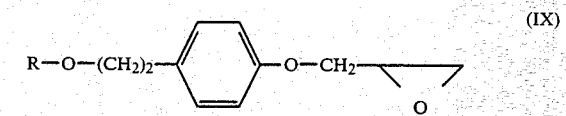
(IX)

and finally reacting the epoxide of general formula IX with an amine R'NH₂ (wherein R' is as hereinbefore defined) to give a compound of general formula (I) wherein X represents a bond.

According to another feature of the invention, the compounds of general formula (I) wherein X represents a bond are prepared by reacting a diazoketone of the formula:

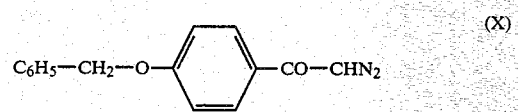
(X)

with a cycloalkanol of the general formula R-OH (wherein R is as hereinbefore defined), reducing the carbonyl radical in the resulting compound of the general formula:

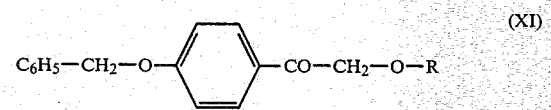
(XI)

to methylene (i.e. —CH₂—) by a method known per se, and debenzylating the cycloalkyloxyethylbenzene compound so obtained to give a phenol of the general formula:

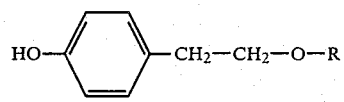

, reacting the phenol derivative with epichlorohydrin to obtain an epoxide of general formula (IX) depicted above and reacting the epoxide with an amine R'NH$_2$ (wherein R' is as hereinbefore defined) to give a compound of general formula (I) wherein X is a bond.

The enantiomers of the compounds of general formula (I) can be obtained either by separation of mixtures thereof with the aid of an optically active acid or, preferably, by the direct reaction of the sodium salt of a phenol of the general formula:

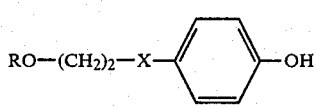

(wherein R and X are as hereinbefore defined) with the desired enantiomer of an oxazolidine derivative of the general formula:

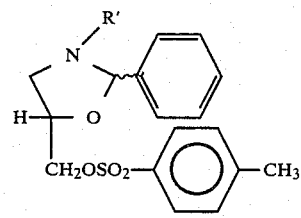

(wherein R' is as hereinbefore defined) in solution in an aprotic solvent, such as dimethylformamide (hereinafter abbreviated to DMF), at a temperature from 30° to 80° C., followed by hydrolysis of the resulting compound in an acid medium.

The optically active oxazolidines of the general formula (XIV) are described in the literature, for example by J. J. Baldwin et al., J. Med. Chem. 20, 1024 (1977).

Pharmaceutically acceptable acid addition salts of 3-phenoxypropan-2-ol derivatives of general formula (I), e.g. methanesulphonates, mandelates, fumarates, malonates, citrates and hydrochlorides, may be obtained by methods known per se, for example by treatment of the 3-phenoxypropan-2-ol base with the appropriate acid in a solvent medium, e.g. an alkanol or ether, or mixtures thereof.

By the term 'methods known per se' in this specification is meant methods heretofore used or described in the literature.

The following Examples illustrate the preparation of 3-phenoxypropan-2-ol derivatives of the present invention.

The analyses and the IR and NMR spectra confirm the structure of the compounds.

EXAMPLE 1

3-[4-(2-Cyclopentyloxyethoxy)phenoxy]-1-isopropylaminopropan-2-ol and its malonate 1. 2-Cyclopentyloxyethanol 200 g (2.32 mols) of cyclopentanol, 38.5 cc (0.77 mol) of ethylene oxide and 2.3 g (0.1 g atom) of sodium metal are introduced at 0° C. into a 500 ml autoclave. The mixture is then heated for 4 hours at 75° C. The autoclave is left to cool and the reaction mixture is then distilled. This gives the title compound, which boils at 90°–92° C. under a pressure of 15 mm Hg.

2. 2-Cyclopentyloxyethyl tosylate

A mixture of 150 cc of pyridine and 38 g of tosyl chloride is cooled to −5° C. 24 g (0.185 mol) of 2-cyclopentyloxyethanol in 100 cc of pyridine are added dropwise at this temperature with stirring. The temperature is then allowed to rise slowly and the reaction mixture is left to stand overnight. It is then poured into a mixture of iced water and 260 cc of concentrated HCl, and extraction is carried out with diethyl ether. The ether phase is washed with water, dried and evaporated to dryness. The tosylate obtained is used as such for the next step.

3. 4-(2-Cyclopentyloxyethoxy)-phenol benzyl ether

A solution of 24 g (0.12 mol) of 4-benzyloxyphenol in 100 cc of DMF is added dropwise to a 50% suspension of 6.2 g (0.132 mol) of NaH in 50 cc of DMF. When the evolution of gas has ended, a solution of 36 g (0.127 mol) of 2-cyclopentyloxyethyl tosylate in 100 cc of DMF is then added. The mixture is stirred for half an hour. It is then heated for 2 hours at 55°–60° C. with stirring. The reaction mixture is poured into iced water. Extraction is carried out with diethyl ether. The ether phase is washed with dilute sodium hydroxide solution and then with water, dried and evaporated to dryness.

4. 4-(2-Cyclopentyloxyethyl)-phenol 36 g (0.115 mol) of the ether obtained as described in 3 above are debenzylated at 45° C., under 50 psi of hydrogen, in 300 cc of methanol, in the presence of 5% Pd-on-charcoal. When the reaction has ended, the catalyst is filtered off and the filtrate is evaporated to dryness. A crude oil is recovered, which is purified by passage through a silica column, elution being carried out with chloroform.

5. 3-[4-(2-(Cyclopentyloxyethoxy)-phenoxy]-1,2-epoxypropane 20 g (0.09 mol) of 4-(2-cyclopentyloxyethoxy)-phenol are stirred with 90 cc of 1N sodium hydroxide solution until a clear solution is obtained, 12.5 g (0.135 mol) of epichlorohydrin are then added and the mixture is stirred for 24 hours at ambient temperature. The reaction mixture is then extracted with diethyl ether. The ether phase is washed with dilute sodium hydroxide solution and then with water, dried over MgSO$_4$ and then evaporated to dryness.

6. 3-[4-(2-Cyclopentyloxyethoxy)-phenoxy]-1-isopropylaminopropan-2-ol malonate 20 g of the crude epoxide obtained in 5 above are heated at the reflux temperature for 20 hours in 150 cc of isopropylamine. The mixture is then evaporated to dryness, the residue is dissolved in dilute hydrochloric acid and extraction is carried out twice with diethyl ether. The aqueous phase is rendered alkaline with sodium hydroxide solution. The base is extracted with methylene chloride. The organic phase is washed with water, dried and evaporated to dryness. The oily base is converted to the neutral malonate, which melts at 96°–98° C. after recrystallisation from an ethanol/diethyl ether mixture.

EXAMPLE 2

3-[4-(2-Cyclopentyloxyethyl)-phenoxy]-1-isopropylaminopropan-2-ol

1. 4-(2-Cyclopentyloxyethyl)-phenol benzyl ether

24.11 g of cyclopentanol and then 1.63 g of sodium are introduced into a 250 ml round-bottomed flask. The mixture is heated at 110°–120° C. until the sodium has disappeared. The mixture is then cooled and 80 cc of benzene are added. 26.77 g of 2-(4-benzyloxyphenyl)ethanol tosylate are then introduced in portions. The mixture is heated at 80° C. for 3 hours. The benzene is driven off, the residue is taken up in water and the solution is extracted with ethyl acetate. This gives an oil.

2. 4-(2-Cyclopentyloxyethyl)-phenol

13.54 g of the compound obtained as described in 1 above are debenzylated in solution in 250 cc of methanol, in the presence of 5% palladium-on-charcoal, under a pressure of 55 psi of hydrogen. The product is obtained after the catalyst has been filtered off and the filtrate has been evaporated.

3. 3-[4-(2-Cyclopentyloxyethyl)-phenoxy]-1,2-epoxypropane

In a 500 ml round-bottomed flask, 8.95 g of the phenol obtained under 2 above are dissolved in 80 cc of sodium hydroxide solution. 17.85 g (0.193 mol) of epichlorohydrin are introduced and the reaction mixture is stirred for 12 hours at ambient temperature. The desired compound is obtained after extraction with diethyl ether, washing with water and drying over magnesium sulphate.

4. 3-[4-(2-Cyclopentyloxyethyl)-phenoxy]-1-isopropylaminopropan-2-ol

In a 250 ml round-bottomed flask, 12.8 g of the epoxide obtained as described in 3 above are heated at the reflux temperature for 11 hours with 50 ml of isopropylamine. The excess amine is removed and the mixture is taken up in water, acidified with dilute HCl and extracted with diethyl ether. The aqueous phase is rendered alkaline with NaOH and extracted with diethyl ether. The organic phase is washed with water, dried over MgSO4 and filtered, and the filtrate is evaporated. After recrystallisation from hexane, the desired product is obtained in the form of the base, which melts at 66° C.

EXAMPLE 3

3-[4-(2-Cyclohexyloxyethyl)-phenoxy]-1-isopropylaminopropan-2-ol and its neutral fumarate

1. Cyclohexyloxymethyl (4-benzyloxyphenyl) methanone

100 g (1 mol) of cyclohexanol and 33 g (0.13 mol) of 4-benzyloxy-2-diazoacetophenone (J. Jeffreys, J. Chem. Soc. (1956), 4451) are introduced into a one liter round bottomed flask. The mixture is heated in a water-bath at 35° C. with magnetic stirring. 4 cc of boron trifluoride etherate are introduced in two portions. The solution is left in the water-bath for 4 hours and the cyclohexane is then driven off under reduced pressure. The product is purified by chromatography on silica, elution being carried out with a 7/3 cyclohexane/ethyl acetate mixture. The product is recrystallised from cyclohexane.

2. 4-(2-Cyclohexyloxyethyl)-phenol

16 g (0.049 mol) of cyclohexyloxymethyl (4-benzyloxyphenyl) methanone are hydrogenated under a hydrogen pressure of 50 psi, at a temperature of 35 to 40° C., in solution in 150 cc of methanol containing a few drops of 70% HClO4 solution and 1 g of 5% palladium-on-charcoal. The catalyst is filtered off, the solvent is evaporated off in vacuo and the residual oil is chromatographed on a silica column (eluent: 8/2 cyclohexane/ethyl acetate). An oil is collected which has a refractive index $n_D^{18} = 1.5335$; boiling point 0.01 = 130° C.

3. 3-[4-(2-Cyclohexyloxyethyl)-phenoxy]-1,2-epoxypropane

13.3 g (0.06 mol) of 4-(2-cyclohexyloxyethyl)-phenol, 3.04 (0.076 mol) of sodium hydroxide pellets and 50 cc of water are introduced into a round-bottomed flask. The mixture is stirred at ambient temperature and, when the solution has become homogeneous, 18.6 g (16 cc, 0.2 mol) of epichlorohydrin are introduced. The stirring is continued at ambient temperature for 16 hours. Extraction is carried out with diethyl ether and the organic phase is washed with water. It is dried over magnesium sulphate and the ether is driven off. This gives an oil, which is used directly in the next step.

4. Neutral fumarate of 3-[4-(2-cyclohexyloxyethyl)-phenoxy]-1-isopropylaminopropan-2-ol

5.6 g (0.019 mol) of 3-[4-(2-cyclohexyloxyethyl)-phenoxy]-1,2-epoxypropane, 40 cc of methanol and 11.73 g (17 cc, 0.198 mol) of isopropylamine are introduced into a 200 cc round-bottomed flask. The mixture is heated in an oil-bath at 50° C. for 7 hours, with magnetic stirring. The methanol is driven off under reduced pressure. The oil is taken up in 40 cc of 3N HCl and extraction is carried out with diethyl ether. The aqueous phase is rendered alkaline and extracted with diethyl ether. The paste is triturated in pentane and petroleum ether, and an oil is recovered.

3.65 g (0.01 mol) of the obtained 3-[4-(2-cyclohexyloxyethyl)-phenoxy]-1-isopropylaminopropan-2-ol are introduced into 30 cc of acetone. 1.16 g (0.01 mol) of fumaric acid in 20 cc of acetone are added to this solution; the final solution is filtered through paper and, after the filtrate has been standing overnight, there is precipitation of white flaky crystals. They are filtered off and washed with 30 cc of acetone. The salt obtained is recrystallised from a minimum amount of acetone.

Its melting point is 100° C.

EXAMPLE 4

(S)(−)-Isomer of 3-[4-(2-cyclopentyloxyethyl)-phenoxy]-1-isopropylaminopropan-2-ol A solution of 7.4 g (0.036 mol) of 4-(2-cyclopentyloxyethyl)-phenol in 10 cc of DMF is added to a 50% suspension of 1.8 g (0.036 mol) of NaH (washed with toluene beforehand) in 10 cc of DMF.

When the formation of the sodium salt of the phenol has ended, a solution of 13.6 g (0.036 mol) of (S)-1-isopropyl-2-phenyl-5-hydroxymethyloxazolidine tosylate in 10 cc of DMF is added and the mixture is then heated to 50°–60° C. The heating is continued for 5 hours, the mixture is cooled and then poured into water, and extraction is carried out with diethyl ether. The ether phase is washed with water, dried and filtered, and the filtrate is evaporated. The residual oil is taken up in water, acidified with 15 cc of concentrated hydrochloric acid, stirred for ½ hour and then extracted with diethyl ether. The aqueous phase is rendered alkaline with concentrated sodium hydroxide solution (20 cc) and extracted with diethyl ether. The ether phase is washed with water, dried over MgSO4 and filtered, and the filtrate is evaporated. This gives an oil from which the hydrochloride is prepared in the following manner:

The oily base is solubilised in a minimum amount of acetone, an insoluble material is removed by filtration, the filtrate is acidified with a solution of hydrogen chloride in diethyl ether, and ether is then added until slight turbidity is obtained. The product crystallises. It is filtered off, dried and recrystallised from an acetone/diethyl ether mixture.

Melting point = 97°–100° C.
$[\alpha]_D = -19.64°$ (c=0.011; CH$_3$OH).

The purified base (cf the title above), obtained by rendering the hydrochloride alkaline, crystallises and melts at 40°–41° C.

3-Phenoxypropan-2-ol derivatives obtained by the procedures of the foregoing Examples are depicted in the following TABLE by reference to general formula (I).

TABLE

| Compound | R | R' | X | Form | Melting Point (°C.) |
|---|---|---|---|---|---|
| 1 | cyclopentyl | isopropyl | O | malonate | 96–98 |
| 2 | cyclopentyl | isopropyl | bond | base | 66 |
| 3 (S) | cyclopentyl | isopropyl | bond | hydrochloride | 97–100 |
| 4 | cyclohexyl | isopropyl | O | hydrochloride | 112 |
| 5 | cyclohexyl | tert-butyl | O | hydrochloride | 138–139 |
| 6 | cyclohexyl | isopropyl | bond | fumarate | 100 |

3-Phenoxypropan-2-ol derivatives of general formula (I) were subjected to a series of pharmacological tests, which demonstrated their valuable properties in the cardiovascular field.

The acute toxicity on oral and intravenous administration was evaluated on CDI male mice having an average weight of 20 g. The mortality was observed over a period of 5 days following the administration of the compounds. The 50% lethal dose (LD 50) was calculated according to Litchfield and Wilcoxon (J. Pharmacol. Exp. Ther. 1944, 95, 99). The LD 50 ranges from 600 to 2000 mg/kg animal body weight, administered orally.

Studies on isolated organs: Isolated auricles were used which had been removed from rats weighing 250 to 350 g and had been kept in Moran's solution (in g/l: NaCl=7.02; KCl=0.42; CaCl$_2$=0.24; MgCl$_2$=0.20; NaHCO$_3$=2.0; glucose=1.8) oxygenated (95% O$_2$–5% CO$_2$) at a temperature of 31° C. The tachycardia and the increase in the contractile force caused by isoprenaline (curve: dose-response to the agonist) were studied before and after the addition of the antagonist (compound (I) or reference substance) and the pA$_2$ of each of them was calculated by the method of Arunlakshana and Schild (Brit. J. Pharmacol. 1959, 14, 48), the pA$_2$ representing the logarithm of the molar concentration of competitive antagonist requiring twice as strong a dose of agonist to cause the same responses as those obtained in the absence of antagonist. The pA$_2$ of the compounds is between 8 and 10.5.

All the compounds of general formula (I) studied possess an inhibiting activity with respect to the cardiac effects of the isoprenaline, but not with respect to the hypotensive effects thereof: they are therefore definitely agents for selectively blocking the $\beta_1$-adrenergic receptors, that is to say the $\beta$-adrenergic receptors located in the heart, and not the $\beta_2$-adrenergic receptors, which are located in the vessels.

The above results show that the compounds of the invention can be used in human and veterinary medicine for cardiovascular diseases and, in particular, for coronary complaints, complaints affecting the myocardium, and heart beat disorders.

Furthermore, the compounds significantly lower the induced intraocular pressure in hypertensive rabbits. The compounds of the invention can therefore also be used for the treatment of glaucoma.

The invention consequently includes pharmaceutical compositions containing, as active principle, the compounds of general formula (I), and their pharmaceutically-acceptable acid addition salts, in association with any excipients suitable for their oral, rectal or parenteral administration. These pharmaceutical compositions can also contain other medicinal substances with which these compounds and their salts are pharmaceutically and therapeutically compatible.

For oral administration, all the pharmaceutical forms suitable for this method of administration are used, that is to say tablets, coated tablets, gelatin capsules, capsules, cachets, and solutions and suspensions to be taken orally, it being possible for the unit dose of the active principle to vary between 5 and 200 mg and the daily dose being between 10 and 500 mg.

For endorectal administration, suppositories are used which contain 2 to 150 mg of active principle and which are administered to the patient at a rate of 1 to 3 per 24 hours.

For parenteral administration, stabilised and buffered injectable solutions are used which are prepared in advance or for immediate use. The dose of active principle per unit dose can vary between 1 and 10 mg and the daily dose is between 3 and 50 mg.

We claim:

1. A method for the treatment of a patient with glaucoma which comprises administering to such patient a 3-phenoxypropan-2-ol derivative, in the form of a racemate or an enantiomer, of the formula:

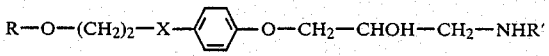

wherein

R is a cycloalkyl radical having 5 or 6 carbon atoms,

X is an oxygen atom or a bond, and

R' is isopropyl or tert.-butyl or a pharmaceutically acceptable acid addition salt thereof, in an amount effective to alleviate the glaucoma condition.

2. The method of claim 1 wherein said derivative is 3-[4-(2-cyclopentyloxyethyl)-phenoxy]-1-isopropylaminopropan-2-ol.

3. The method of claim 1 wherein said derivative is the (S)(−) isomer of 3-[4-(2-cyclopentyloxyethyl)-phenoxy]-1-isopropylaminopropan-2-ol.

4. The method of claim 1 wherein said derivative is 3-[4-(2-cyclopentyloxyethoxy)-phenoxy]-1-isopropylamino-propan-2-ol.

5. The method of claim 1 wherein said derivative is 3-[4-(2-cyclohexyloxyethyl)-phenoxy]-1-isopropylamino-propan-2-ol.

* * * * *